(12) United States Patent
DiBiasio et al.

(10) Patent No.: US 9,844,394 B2
(45) Date of Patent: *Dec. 19, 2017

(54) INSTRUMENT PORT FOR MINIMALLY INVASIVE CARDIAC SURGERY

(71) Applicants: Children's Medical Center Corporation, Boston, MA (US); Massachusetts Institute of Technology, Cambridge, MA (US)

(72) Inventors: Christopher DiBiasio, North Providence, RI (US); Keith Durand, Somerville, MA (US); Jonathan Brigham Hopkins, Salt Lake City, UT (US); Zach Traina, Hingham, MA (US); Alexander Slocum, Bow, NH (US); Samir Nayfeh, Shrewsbury, MA (US); Pedro J. del Nido, Lexington, MA (US); Nikolay V. Vasilyev, Belmont, MA (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/792,916

(22) Filed: Mar. 11, 2013

(65) Prior Publication Data
US 2013/0261400 A1    Oct. 3, 2013

Related U.S. Application Data

(63) Continuation of application No. 12/159,784, filed as application No. PCT/US2007/000270 on Jan. 5, 2007, now Pat. No. 8,394,015.

(Continued)

(51) Int. Cl.
*A61B 17/02* (2006.01)
*A61B 17/34* (2006.01)
(Continued)

(52) U.S. Cl.
CPC ...... *A61B 17/3498* (2013.01); *A61B 17/0218* (2013.01); *A61B 17/3421* (2013.01);
(Continued)

(58) Field of Classification Search
CPC ............ A61B 17/0218; A61B 17/3421; A61B 17/3498; A61B 2017/00876;
(Continued)

(56) References Cited

U.S. PATENT DOCUMENTS 2,243,992 A * 6/1941 Wappler ............... A61B 1/2736
600/153
2,767,705 A * 10/1956 Moore ............... A61B 1/00094
600/114

(Continued)

FOREIGN PATENT DOCUMENTS

WO    98/24501    6/1998
WO    2005/051175    6/2005

OTHER PUBLICATIONS

International Search Report & Written Opinion, PCT/US07/00270, dated Oct. 1, 2007, 11 pages.
(Continued)

*Primary Examiner* — Elizabeth Houston
*Assistant Examiner* — Rachel S Highland
(74) *Attorney, Agent, or Firm* — Fish & Richardson P.C.

(57) ABSTRACT

The instrument ports for introducing instruments into a surgical site that are disclosed herein include a port body having a channel running therethrough from a proximal end to a distal end, an instrument sleeve in slidable contact with the channel, creating a gap therebetween, and a fluid flow
(Continued)

element for removing emboli efficiently from the instrument port, wherein the fluid flow element includes the gap. Disclosed fluid flow systems are for use in the disclosed instrument ports. Methods are also disclosed for removably securing an instrument sleeve to a port body by anchoring the instrument port to heart tissue, making at least one flood line in a channel, flushing out emboli, and performing surgery with the instrument port.

15 Claims, 8 Drawing Sheets

Related U.S. Application Data

(60) Provisional application No. 60/866,255, filed on Nov. 17, 2006, provisional application No. 60/756,385, filed on Jan. 5, 2006.

(51) Int. Cl.
*A61B 17/00* (2006.01)
*A61B 90/00* (2016.01)
*A61B 90/30* (2016.01)

(52) U.S. Cl.
CPC ...... *A61B 17/3423* (2013.01); *A61B 17/3462* (2013.01); *A61B 90/06* (2016.02); *A61B 2017/00119* (2013.01); *A61B 2017/00243* (2013.01); *A61B 2017/00876* (2013.01); *A61B 2017/0243* (2013.01); *A61B 2017/347* (2013.01); *A61B 2017/3445* (2013.01); *A61B 2017/3488* (2013.01); *A61B 2090/306* (2016.02); *A61B 2090/3614* (2016.02); *A61B 2090/373* (2016.02); *A61B 2090/3925* (2016.02); *A61B 2217/005* (2013.01); *A61B 2217/007* (2013.01)

(58) Field of Classification Search
CPC .... A61B 2017/00119; A61B 2017/347; A61B 2017/00243; A61B 2017/3488; A61B 2017/3445; A61B 19/46; A61B 2217/005; A61B 2017/0243; A61B 17/3462; A61B 2217/007; A61B 2019/5425; A61B 1/31; A61B 1/32; A61B 17/3417; A61B 17/3423; A61B 2017/3425; A61B 2017/3427; A61B 2017/3441; A61M 29/00
USPC ..... 600/184, 187, 155, 158; 604/104, 164.1, 604/539, 118, 119, 158; 606/1, 108
See application file for complete search history.

(56) References Cited

U.S. PATENT DOCUMENTS

| | | | |
|---|---|---|---|
| 4,201,199 A * | 5/1980 | Smith | A61B 1/303 600/121 |
| 4,233,982 A * | 11/1980 | Bauer | A61B 17/3498 251/149.2 |
| 4,535,773 A * | 8/1985 | Yoon | A61B 17/3496 600/566 |
| 5,441,503 A | 8/1995 | Considine et al. | |
| 5,797,960 A | 8/1998 | Stevens et al. | |
| 5,842,971 A * | 12/1998 | Yoon | 600/101 |
| 5,899,915 A | 5/1999 | Saadat | |
| 5,928,218 A | 7/1999 | Gelbfish | |
| 6,033,426 A * | 3/2000 | Kaji | A61B 17/3423 600/207 |
| 6,129,713 A | 10/2000 | Mangosong et al. | |
| 6,178,346 B1 | 1/2001 | Amundson et al. | |
| 6,293,282 B1 * | 9/2001 | Lemelson | 128/899 |
| 6,554,793 B1 * | 4/2003 | Pauker | A61B 1/00151 604/158 |
| 6,641,562 B1 * | 11/2003 | Peterson | A61M 5/14244 604/132 |
| 6,689,085 B1 * | 2/2004 | Rubenstein | A61M 1/1003 604/8 |
| 8,951,275 B2 | 2/2015 | Cannon et al. | |
| 2002/0026094 A1 | 2/2002 | Roth | |
| 2002/0111585 A1 * | 8/2002 | Lafontaine | A61M 39/0606 604/167.06 |
| 2004/0111019 A1 * | 6/2004 | Long | A61B 1/00156 600/407 |
| 2004/0116897 A1 * | 6/2004 | Aboul-Hosn | 604/508 |
| 2005/0234296 A1 * | 10/2005 | Saadat et al. | 600/129 |
| 2005/0234298 A1 | 10/2005 | Kucklick et al. | |
| 2007/0197896 A1 * | 8/2007 | Moll et al. | 600/407 |
| 2009/0275893 A1 | 11/2009 | Dibiasio et al. | |

OTHER PUBLICATIONS

Extended European Search Report issued in EP07716358.2 dated Apr. 24, 2014.
Office Action, U.S. Appl. No. 12/159,784 dated Jan. 3, 2012, 9 pages.
European Office Action in European Application No. 07716358.2, dated Oct. 12, 2016, 7 pages.

* cited by examiner

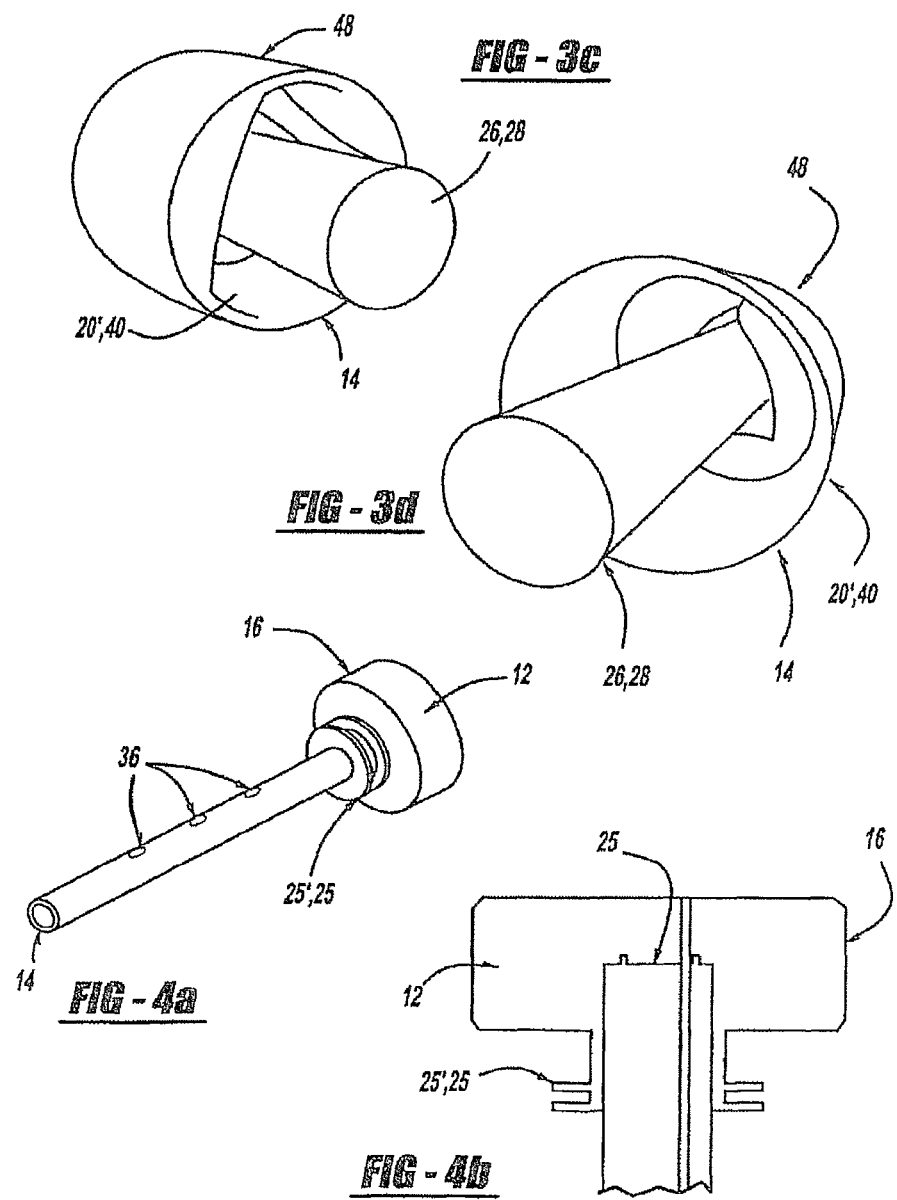

INSTRUMENT PORT FOR MINIMALLY INVASIVE CARDIAC SURGERY

This application is a continuation application and claims priority under 35 U.S.C. §120 from U.S. patent application Ser. No. 12/159,784 (U.S. Pat. No. 8,394,015 to be issued on Mar. 12, 2013), which is a national phase filing under 35 U.S.C. 371, of International Application No. PCT/US07/00270, filed on Jan. 5, 2007, which claims the benefit of priority of U.S. Provisional Patent Application Ser. No. 60/866,255, filed on Nov. 17, 2006 and U.S. Provisional Patent Application Ser. No. 60/756,385, filed on Jan. 5, 2006, the entire contents of all of which are incorporated herein by reference.

STATEMENT REGARDING FEDERALLY SPONSORED RESEARCH OR DEVELOPMENT

This invention was made with government support under the U.S. Department of the Army, Grant No. W81XWH-07-2-0011. The government has certain rights in the invention.

BACKGROUND OF THE INVENTION

1. Technical Field

The present invention relates to methods and instruments used in minimally invasive surgical procedures. In particular, the present invention relates to an instrument port including a flushing system to prevent the introduction of emboli into a surgical site.

2. Description of the Related Art

It is generally accepted that minimally invasive cardiac procedures are more desirable than open heart procedures. Open heart surgery generally requires sawing open the patient's sternum to gain access to the heart. During this surgery, the heart is stopped while catheters and other instruments are inserted into the veins and arteries of the heart. Open heart surgery causes trauma to the patient's chest. In contradistinction, minimally invasive procedures do not require direct access to the heart and almost always provide the patient with shorter recovery times and substantially less pain.

There are three different types of minimally invasive cardiac procedures: Minimally Invasive Direct Coronary Bypass (MIDCAB), Off-Pump Coronary Artery Bypass (OPCAB), and Robotic Assisted Coronary Artery Bypass (RACAB). The MIDCAB procedure is used to remove blockages from the front of the heart and does not require splitting the sternum. A small incision is made in the chest, the muscles are moved, and a small piece of the costal cartilage is removed to gain access to the heart. A heart-lung machine is also commonly used during this procedure. The OPCAB procedure is generally the same as the MIDCAB; however, a heart-lung machine is not used. In both of these procedures, a device can be used to restrict movement of the heart so that it can still beat during the operation. RACAB also does not require the sternum to be cut, and the patient is operated on by robots that are controlled by surgeons. Each of these procedures results in a lower risk to the patient of stroke, lung or kidney problems, and lack of mental clarity, as well as a faster recovery time and lower hospital costs.

Endoscopic surgery can be utilized with each of the above procedures, especially with RACAB. An endoscope is a tubular optical system for viewing the interior of an organ or body cavity. By making a small incision, a hollow tube, or port, can be inserted into the patient to a site of surgery or tissue area, and an endoscope can be inserted into that port for observation and monitoring during surgery. Various other incisions and ports can be created for the insertion of various instruments such as instruments for manipulation, grasping, cutting, and coagulation for use during surgery.

While some open surgical procedures have been adapted to endoscopic techniques, there are limitations, particularly with more complex procedures. Fundamental problems relate to the access ports used for inserting the various manipulative instruments. While limiting incisional trauma, the small diameter of these ports limits the size and design of the inserted instruments. To achieve similar function as in open surgery, equipment becomes complex and therefore more expensive. There is also added risk with each inserted port because each port requires puncturing the body wall, risking injury to contained viscera with each puncture.

Equally important has been the impact on the surgeon's ability to manipulate tissue. While the visual field may have been improved, tactile sensation, depth perception, and proprioceptive awareness of tissues have been markedly reduced by instruments that insulate the surgeon from the operative field. Furthermore, the limited access enabled by each port dictates that multiple ports be used. As procedural complexity increases, the surgeon must adapt to a continuously changing and less predictable environment. Further, as the number of ports increases, the risk and incidence of complications increases. The requirement for highly skilled and coordinated surgical teams also increases. This has resulted in long learning curves and has limited wide application of these procedures for complex cases.

A trocar is commonly used to puncture the body wall to aid in the introduction of ports that allow for the insertion of endoscopes and instruments into the body cavity. The trocar has a sharp end designed to pierce the skin as the surgeon presses it down. It may also pierce the underlying viscera unless great care is taken, particularly in view of the flexibility of the body wall. The trocar includes a cannula or tube used for drainage or for the insertion of an instrument into the body cavity. Since it is desirable to minimize the patient's wounds, there is an effort made to minimize the size of an incision associated with trocar use. As a result, the size of the cannula used in the trocar-created incision is generally small. It therefore can only be used to pass relatively small instruments into the body cavity. Moreover, the narrow cannula severely restricts maneuverability of the device contained therein. Therefore, though trocars offer the advantage of wound minimization, they are of some danger to the viscera, they are of restricted dimensions for allowing the passage of instruments of interest therethrough, and they permit limited tactile manipulation.

HeartPort, Inc. created an integrated system of cannulae and catheters to reach the patient's heart. The system enabled the manipulation of instruments through small ports between the ribs. However, there were several problems with their system. First, the patient still had to undergo cardiopulmonary bypass (CPB) in order to have the minimally invasive cardiac procedure performed. More importantly, however, was that air introduced by instruments into the arrested heart had to be removed prior to restarting the heart. If this air was not removed, the patient could suffer serious medical complications such as a stroke. The Heart-Port, Inc. system had no way of removing/degassing air from inserted instruments or from pockets formed in the arrested heart.

Research recently showed that it is possible to perform minimally invasive cardiac procedures on beating hearts (Suematsu, et al., "Three-dimensional echocardiographyguided atrial septectomy: An experimental study," Journal of Thoracic and Cardiovascular Surgery (2004) 128: 53-59). In order to make such a surgery feasible, a device is needed that prevents air from entering the chambers of the heart, as these emboli could cause a stroke in a patient.

U.S. patent application Ser. No. 10/580,144 to Cannon and del Nido discloses a trocar including an insertion end having a fluid and air-tight chamber. The chamber is made fluid and air-tight via a sealing device. The trocar also includes an agitator to move air or foreign objects from the insertion end to an opposite end so as to keep the air or foreign objects away from the body into which the trocar is inserted. Two lumens are located within the trocar: an instrument lumen and a downflow lumen. An inlet port allows for the flow of inert fluid through the downflow lumen and out through an outlet port proximate to the instrument lumen to force out any air bubbles in the trocar away from the insertion end.

There is therefore a need for a method for introducing surgical tools and/or imaging equipment into the chambers of a still-beating or arrested heart. There is a further need to eliminate the introduction of air into the chambers of the heart during the course of the surgery. There is also a need to limit the amount of blood lost from the heart chamber into the chest cavity of the patient, as well as limit blood flow into the instrument through a trocar while in the operating room. There is further a need to make the instrument port compatible with current imaging techniques, such as 3-D ultrasonic imaging, to allow the instrument port to be easily visualized during minimally invasive procedures.

SUMMARY OF THE INVENTION

The present invention provides an instrument port for introducing instruments into a surgical site, including a port body having a channel running therethrough from a proximal end to a distal end of the port body, an instrument sleeve in slidable contact with the channel, creating a gap therebetween, and a fluid flow mechanism for removing emboli efficiently from the instrument port, wherein the fluid flow mechanism creates the gap.

Also provided is an instrument sleeve for holding an instrument inside an instrument port, the instrument sleeve designed to fit around an instrument such that when the instrument is inside the instrument sleeve, an interface is created, and the instrument sleeve further includes a standard outer diameter capable of fitting inside any instrument port.

Further provided is a tissue anchoring mechanism for anchoring an instrument port to tissue, and an end sealing device for compliantly sealing an instrument port.

The present invention further provides a fluid flow system for use in the instrument port including a gap between an outer surface of an instrument sleeve and an inner surface of a channel, fluid inlet device for adding fluid to the gap, and fluid outlet device for removing fluid from the gap.

The present invention provides methods for removably securing an instrument sleeve to a port body of the instrument port, anchoring the instrument port to heart tissue, making at least one flood line in a channel in the gap of the instrument port, flushing out emboli from the instrument port, and performing surgery using the instrument port.

BRIEF DESCRIPTION ON THE DRAWINGS

Other advantages of the present invention will be readily appreciated as the same becomes better understood by reference to the following detailed description when considered in connection with the accompanying drawings, wherein.

Figure 5A:
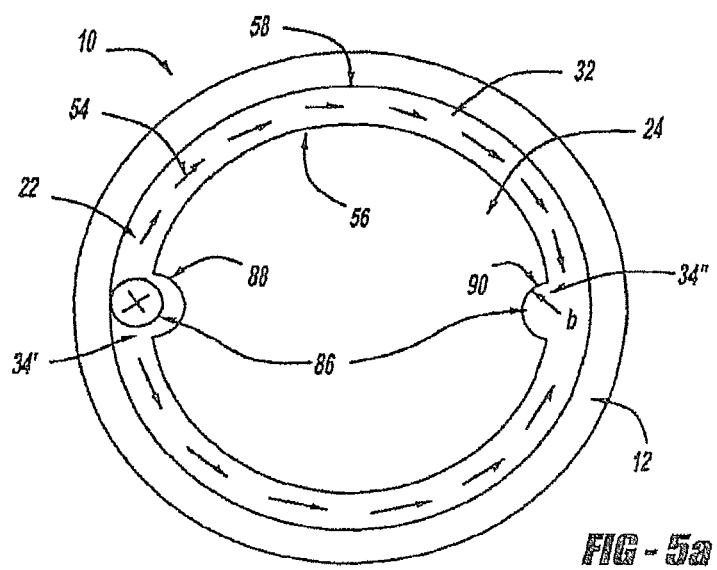
Figure 5B:
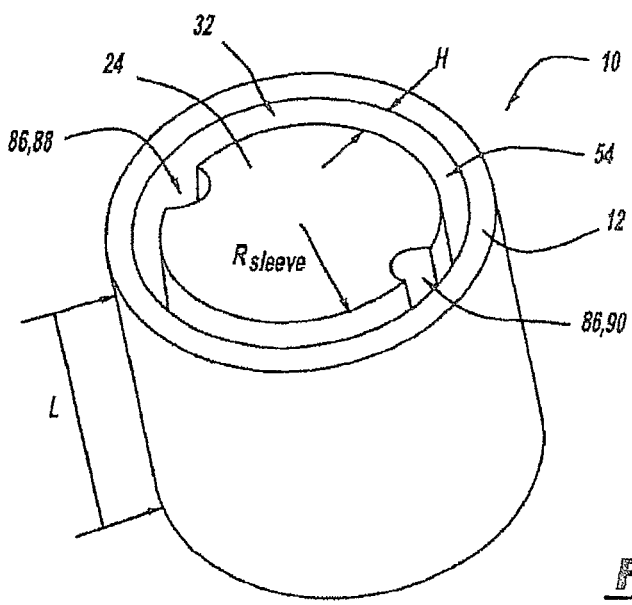
Figure 6:
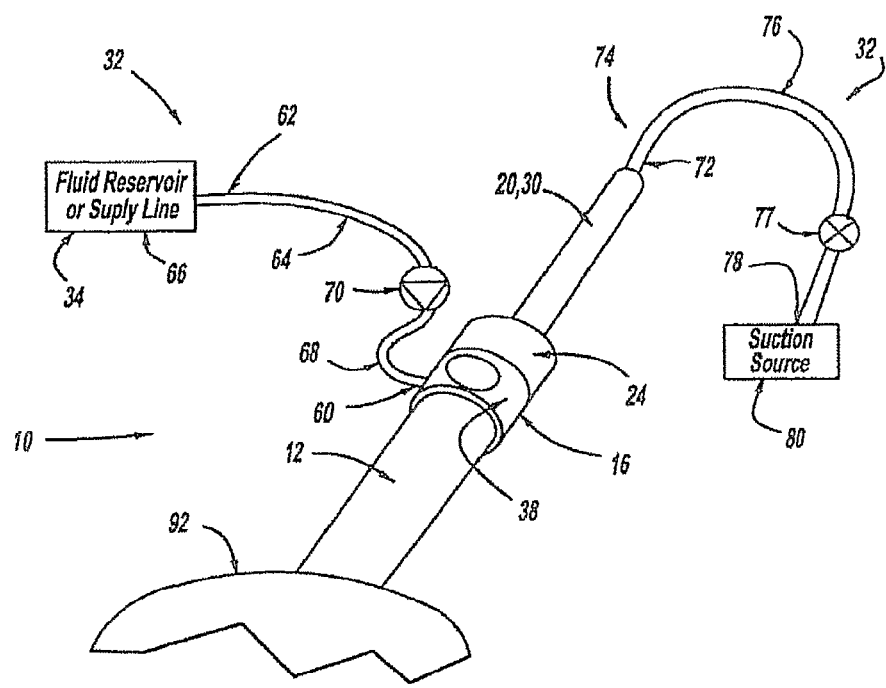
Figure 7:
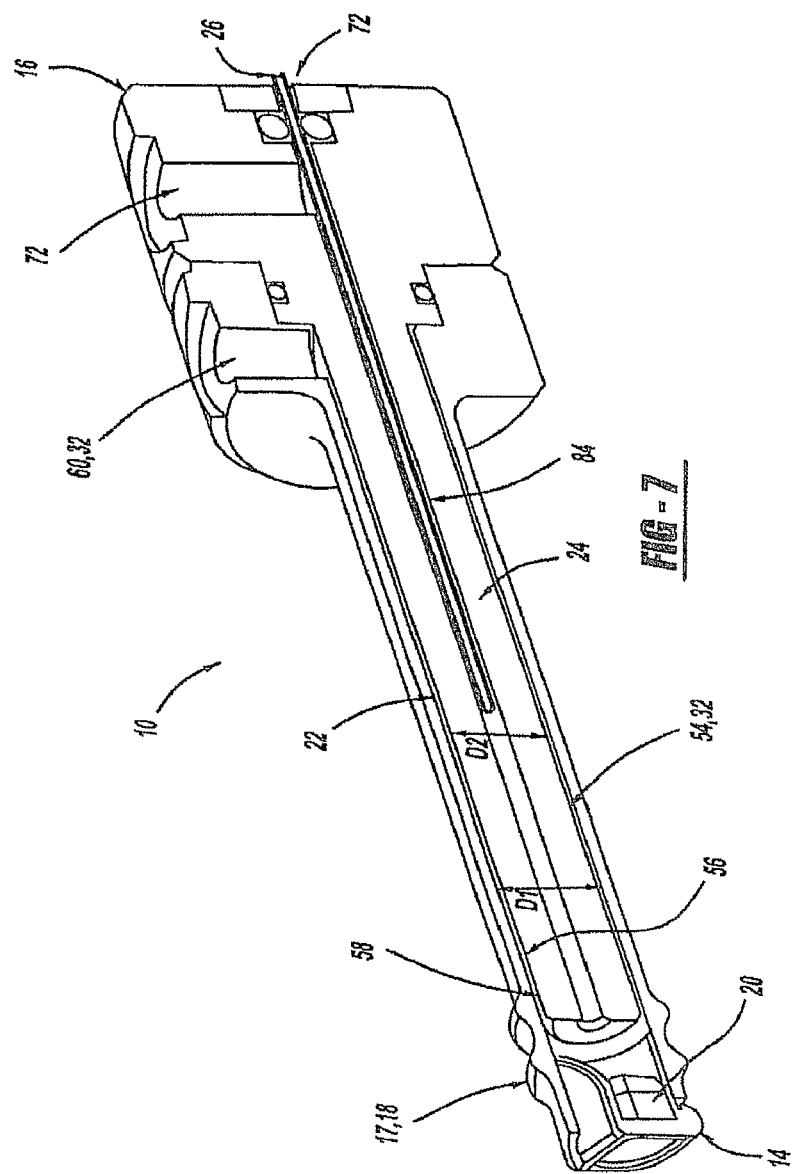
Figure 8:
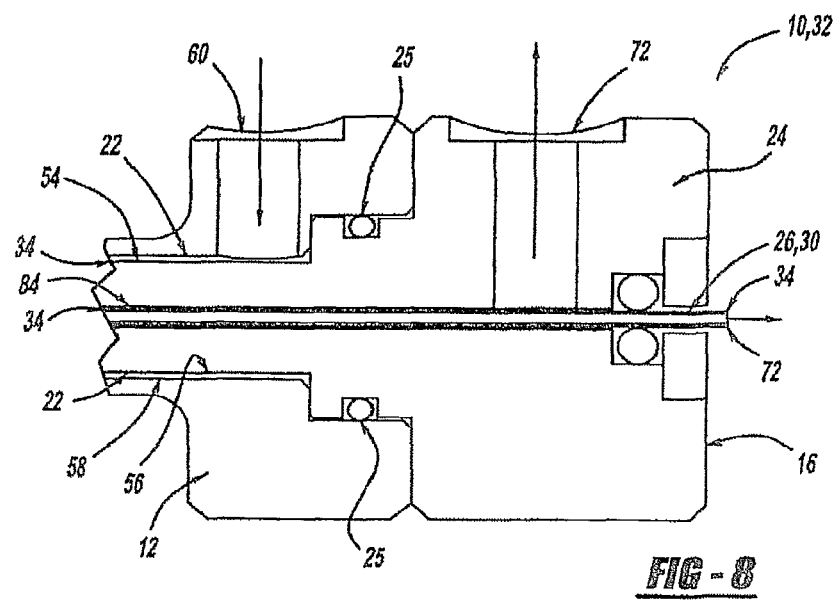
Figure 9:
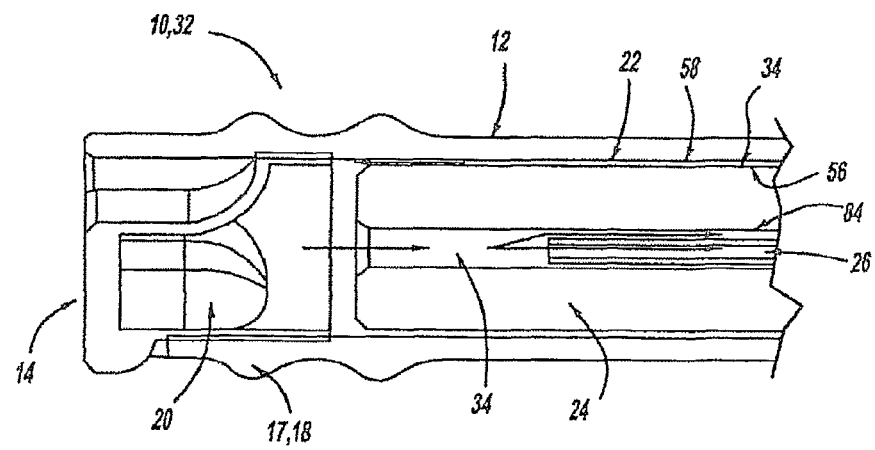
Figure 10:
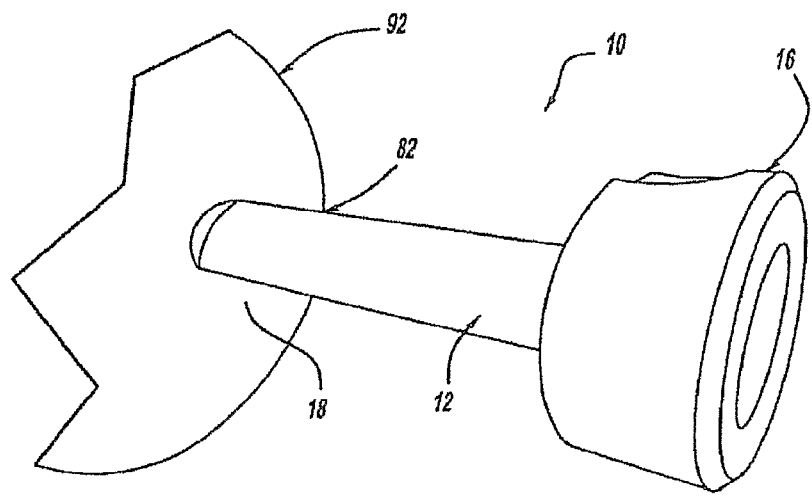
Figure 11:
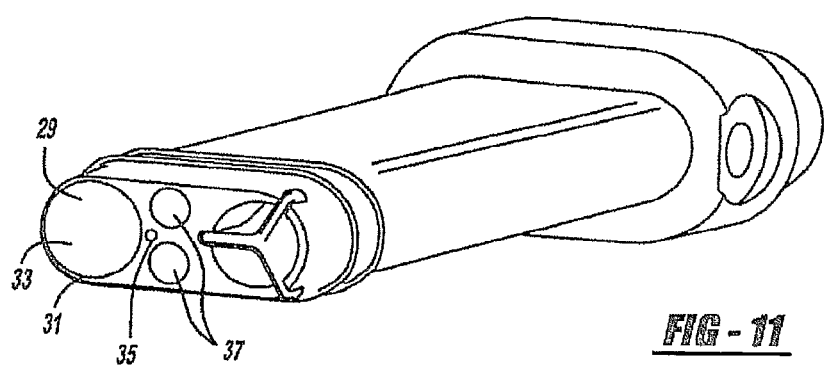

FIGS. 3a, 3b, 3c, and 3d are 3-D representations of a second embodiment of the end sealing mechanism interfacing with an instrument;

FIG. 4a is a 3-D view and FIG. 4b is a cross-sectional view of the instrument sleeve 24 with flexural ribs as the second embodiment of the sleeve sealing mechanism;

FIG. 5a is a cross-sectional view and FIG. 5b is a 3-D cross-sectional view of the gap between the channel and instrument sleeve creating two fluid channels;

FIG. 6 is a representation of the fluid flow system of the present invention;

FIG. 7 is a 3-D cross-sectional view of the fluid flow system of the present invention;

FIG. 8 is a cross-sectional view of a close-up of "View A" of FIG. 7;

FIG. 9 is a cross-sectional view of a close-up of "View B" of FIG. 7;

FIG. 10 is a 3-D view of the instrument port of the present invention interfaced with the human heart; and FIG. 11 is a three-dimensional view of an embodiment of the instrument port of the present invention.

DETAILED DESCRIPTION

The present invention provides an apparatus for the introduction of surgical tools and imaging equipment into the chambers of an arrested or still-beating heart that prevents air from entering the chambers of the heart, thereby preventing an embolism.

An "instrument port" is defined herein as a trocar-like structure that includes a hollow center for receiving surgical instruments.

An "embolus" is defined herein as an item that travels through the bloodstream, lodges in a blood vessel and blocks it. Examples of emboli are a detached blood clot, a clump of bacteria, and foreign material such as air. Throughout the application, reference is made to emboli that are air bubbles; however, any other emboli can be substituted without deviating from the spirit of the invention.

Like structure in the different embodiments is indicated by primed numbers.

Figure 1:
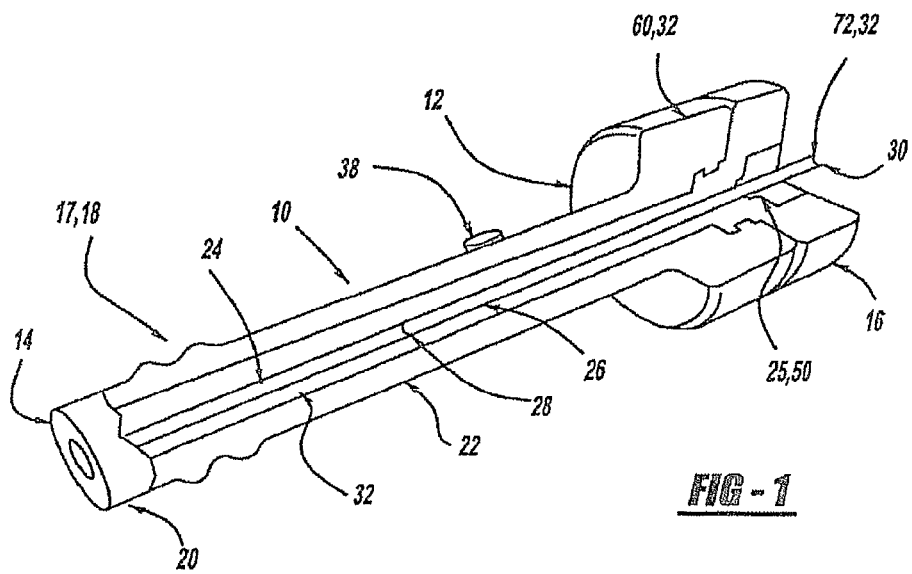
FIG. 1 is a three-quarter section isometric view of the instrument port of the present invention.

As shown generally in FIG. 1, an instrument port 10 is provided for introducing instruments into a surgical site, including a port body 12 having a channel 22 extending therethrough from a proximal end 14 to a distal end 16 of the port body 12, an instrument sleeve 24 in slidable contact with the channel 22, creating a gap 54 therebetween, and a fluid flow system 32 for removing emboli efficiently from the instrument port 10, wherein the fluid flow system 32 flows through the gap 54.

The instrument port 10 is generally formed of a biocompatible material that is approved by the United States Food and Drug Administration for use in surgical procedures. The material is preferably durable and capable of being sterilized completely for subsequent re-use. Alternatively, the instrument port 10 can be constructed as a disposable one-time or throw-away device without the need for subsequent sterilization. Preferably, the instrument port 10 is made from an FDA approved polymer plastic, such as polyvinylidene fluoride, sold under the tradename KYNAR by Pennsalt Chemicals Corporation, that is both highly ultrasound visible as well as dimensionally stable. Further, KYNAR® is also highly wetting so that when using a water-based flushing agent, the wetting nature encourages bubbles to detach from surfaces and be flushed from the instrument port 10. This is preferable because it eliminates air bubbles or other emboli present in the instrument port 10 from entering into the patient's heart and causing embolism. Other materials known to those of skill in the art as being ultrasound visible or highly wetting can also be used. Alternatively, materials that are not ultrasound visible can be used with ultrasonic markers 36 operatively attached to the port body 12 in order to enhance the visualization of the port body 12 when using 3-D ultrasound, as shown in FIG. 5a. Sensors 38 can also be operatively attached to the port body 12 to allow for visualization of heart structures for guiding surgery, shown in FIG. 1. Sensors 38 are also discussed further herein.

The proximal end 14 of the instrument port 10 can be either sharp to cut through tissue or blunt. A sharp proximal end 14 requires care in insertion and movement of the instrument port 10 so as not to unnecessarily damage surrounding tissue. A blunt proximal end 14 can be used when an incision has already been made in the patient.

The proximal end 14 includes a tissue anchoring mechanism 17, such as a ribbed heart tissue anchor 18. The ribbed heart tissue anchor 18 is generally a series of ribs along the proximal end 14 of the port body 12. Preferably, there are at least two ribs 19 protruding from the port body 12. The ribs 19 are spaced an appropriate distance apart to firmly anchor the heart tissue 92 to the instrument port 10. The ribs 19 can be located at any suitable distance along the proximal end 14 of the port body 12. The ribs 19 are preferably in a rounded shape as to not cause stress to the heart tissue 92 as the instrument port 10 is inserted. The ribbed heart tissue anchor 18 can be molded in a fixed position or can be adjustably attached to the port body 12 such that the ribs 19 can be moved along the length of the port body 12. In other words, the ribs 19 can be formed as one with the port body 12 or can be affixed to the port body 12. Examples of affixable ribs include, but are not limited to, an o-ring or a frictionally engaged sleeve.

Figure 2A:
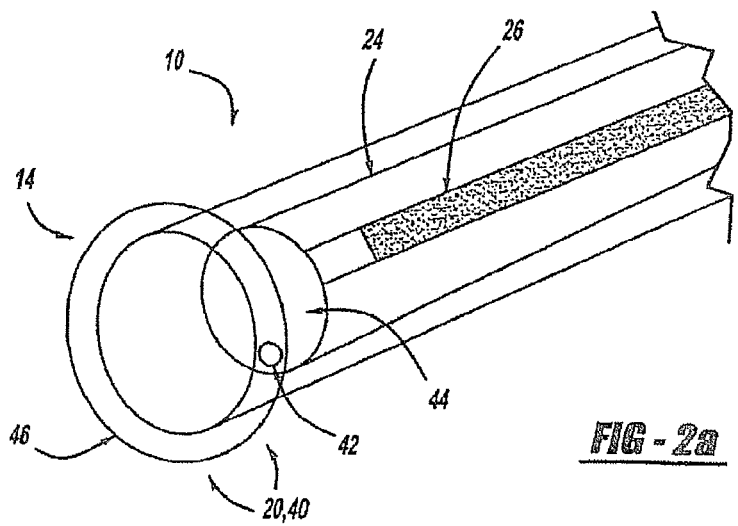
FIGS. 2a and 2b are side views of the instrument port with a first embodiment of the end sealing mechanism.
Figure 2B:
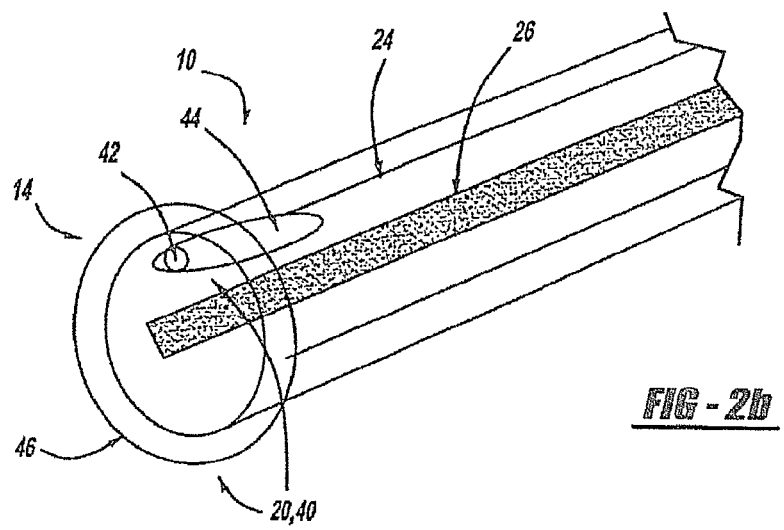
Figure 3A:
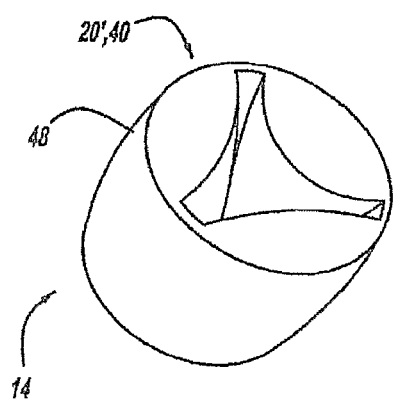
Figure 3B:
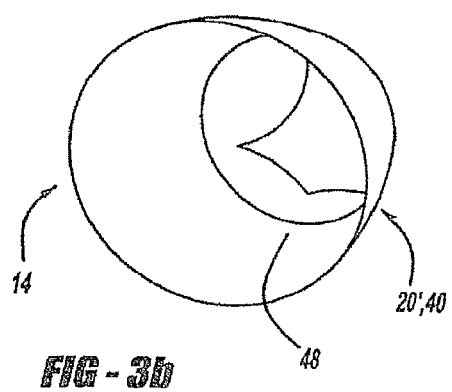

The proximal end 14 of the port body 12 can also include an end sealing mechanism 20. The end sealing mechanism 20 prevents material from entering or exiting the instrument port 10 before an instrument 26 is inserted while also allowing access to the interior of the heart after insertion of an instrument 26 into the instrument sleeve 24. Preferably, the end sealing mechanism 20 is a check valve 40. The check valve 40 is a compliant flexure that opens when pushed by an operative end 28 of the instrument 26, but seals again once the operative end 28 of the instrument 26 is removed. The check valve 40 can be made of material such as, but not limited to, strong polyester films, sold under the tradename MYLAR by DuPont, or silicone rubber. For example, as shown in FIGS. 2a and 2b, a magnet 42 operatively attached to a check flap 44 can be used to provide an attractive force to a ferromagnetic ring 46 made of steel or any other suitable material operatively attached to the proximal end 14 of the port body 12. The magnet 42 has a sufficient force to allow the magnet 42 to remain in a closed position unless an instrument 26 is in use. In a second embodiment of the end sealing mechanism 20', an end sealing mechanism such as, but not limited to a tri-leaflet or tri-cuspid valve 48, is shown in FIGS. 3a-d. The valve 48 remains closed even when there is negative pressure in the heart. Such valves 48 are modeled after the mitrial valve in the human heart, and can be made with any suitable material such as rubber or other materials known to those of skill in the art. When a positive pressure is applied to the underside of the valve 48, it behaves as a check valve. The valve 48 is large enough to allow the operative end 28 of the instrument 26 to pass through and enter the heart. The valve 48 has a sufficient closing force to remain closed unless the instrument 26 is in use. Thus the check valve 40 seals the port from the interior of the heart when exposed to higher pressures, thereby enabling the port to be used in both ventricular and atrial operations.

The port body 12 further includes a channel 22 extending through the length of the port body 12 from the proximal end 14 to the distal end 16. The channel 22 receives the instrument sleeve 24. Preferably, the channel 22 has a standard-sized inside diameter D1 sufficient for accommodating the instrument sleeve 24. Alternatively, the inside diameter D1 can vary based upon the size of each instrument 26 to be inserted in combination with the instrument sleeve 24. The instrument port 10 is designed such that the total amount of blood lost during insertion and removal of the instruments 26 is limited to the flush volume of the channel 22, which is well below the body's tolerance for blood loss, even after several instrument exchanges.

The instrument sleeve 24 is in slidable contact with the channel 22 such that the instrument sleeve 24 can be inserted and readily removed from the instrument port 10 without difficulty. The instrument sleeve 24 provides a custom seal around each instrument 26. That is, each instrument sleeve 24 is designed to fit around a particular instrument 26. An interface 84 is created between the instrument sleeve 24 and the instrument 26 that allows for fluid to pass through from the operative end 28 to a manipulative end 30 of the instrument 26 when the fluid flow system 32 is in use, thus removing emboli. The emboli cannot easily travel through the interface when the fluid flow system 32 is not in use. An outer diameter D2 of the instrument sleeve 24 fits within a standard channel 22. Each instrument sleeve 24 can fit instruments 26 of varying sizes while still substantially filling the channel 22, creating a mating interface to the channel 22 that is identical to each instrument 26 used as well as creating part of the fluid flow system 32 used to flush out any trapped air, discussed later herein. Such a design enables the end sealing mechanism 20 to achieve a robust and secure seal regardless of the instruments inserted therein. The instrument sleeve 24 is made of any suitable material such as, but not limited to, polyvinylidene fluoride, sold under the tradename KYNAR by Pennwalt, or polytetrafluoroethylene (PTFE), the homopolymer of tetrafluoroethylene sold under the trademark TEFLON by DuPont.

The instrument sleeve 24 is removably sealed within the port body 12 via a sleeve sealing mechanism 25. In a first embodiment, the sleeve sealing mechanism 25 is an o-ring 50, as shown in FIG. 1. In a second embodiment, the sleeve sealing mechanism 25' is a series of flexural ribs 52, as shown in FIGS. 4a and 4b. The flexural ribs 52 can be formed as part of the instrument sleeve 25 or can be added as an additional part. Alternative sleeve sealing mechanisms 25 known to those of skill in the art can be used without departing from the spirit of the present invention. For example, experiments showed that interference fits between a KYNAR® port body 12 and a TEFLON® instrument sleeve 24 provided no leakage above critical parameter values.

The instrument 26 can be any instrument capable of use in minimally invasive surgery. The instrument 26 is preferably made of biocompatible materials. Examples of such instruments 26 include, but art not limited to, a light source, dissectors, graspers, scissors, needle holders, fan retractors, cautery instruments, insufflation needles, and forceps. The instrument 26 can be removably sealed with an instrument sealing mechanism 27 within the instrument sleeve 24 in the same manner as the instrument sleeve 24 is sealed within the port body 12, i.e. via an o-ring, flexural ribs, or any other suitable sealing mechanism known to those of skill in the art.

Additionally, as shown in FIG. 11, the port body 12 can also accept an imaging sleeve 29. The imaging sleeve 29 is identical to the instrument sleeve 24 except that instead of enabling the insertion of instruments, the imaging sleeve 29 enables imaging equipment to be brought into close proximity of the location of surgery. Preferably, the imaging sleeve 29 is approximately 2-8 mm; however, other sizes can be utilized without departing from the spirit of the present invention. The imaging sleeve 29 is sized to accommodate numerous imaging tools that can include, but are not limited to, fiber optic, near infra-red, ultrasonic transducers, and other imaging devices known to those of skill in the art. The imaging sleeve 29 has an insertion end 31 at the proximal end 14 of the port body 12. At the insertion end 31 the imaging sleeve 29 is capped with a transparent, flexible, dome-shaped bulb 33. The bulb 33 both protects the tool from the environment and provides a clear imaging medium, while allowing the tool to conform to the imaged surface. Furthermore, the function of the imaging tools is augmented with the addition of a saline flush line 35, which is fitted with a check valve 40' to ensure one-way flow. The flush line 35 rinses the area directly in front of the imaging sleeve 29, thus providing a clear optical line of sight. Two small holes 3 mm in diameter allow for the addition of fiber optic illumination, for added light when imaging, or the addition of ultrasonic transducers to be combined with another imaging technology.

The fluid flow system 32, designed to remove emboli, is created by the gap 54 between an outer surface 56 of the instrument sleeve 24 and an inner surface 58 of the channel 22, as shown in FIGS. 5a and 5b. In other words, the sizes of the inner diameter D1 of the port body 12 and outer diameter D2 of the instrument sleeve 24 are slightly different so as to create the gap 54. The fluid flow system 32 is further shown in FIGS. 6-9. A fluid inlet 60 is operatively connected to the distal end 16 of the port body 12 and is in fluid connection with the gap 54 to allow fluid 34 to enter into the gap 54. A distal end 62 of a fluid inlet line 64 is operatively connected to a fluid source 66, and a proximal end 68 of the fluid inlet line 64 is operatively connected to the fluid inlet 60 to supply fluid to the instrument port 10. The fluid inlet line 64 can further include a check valve 70 for control purposes.

A fluid outlet 72 is operatively connected to the manipulative end 30 of the instrument 26. A proximal end 74 of a suction line 76 can be operative attached to the fluid outlet 72 to aid in the removal of the fluid 34, while a distal end 78 of the suction line 76 can be operatively attached to a suction source 80. The suction line 76 can further include a valve 77 for control purposes.

Sensors 38 can be included in the instrument port 10 to control the flushing process by automation, turning on the flushing sequence when the instrument 26 is fully inserted within the instrument sleeve 24 but while the end sealing mechanism 20 is still in a closed position. The sensors 38 can be electronic, for example digital sensors using CMUT or similar technology, or a mechanical switch. The sensors 38 can also be used to alert a surgeon to the presence of air bubbles in the instrument port 10.

The fluid 34 circulated through the fluid flow system 32 is preferably biocompatible, readily absorbed into the blood stream, and contains no bubbles. For example, the fluid 34 can be saline solution, such as fluids for parenteral use containing metallic salts, sold under the tradename Plasma-Lyte by Baxter Laboratories, Inc., any other suitable electrolyte solution, or carbon dioxide.

The purpose of the fluid flow system 32 is to flush any trapped emboli from the instrument port 10 before using an instrument 26 at an operating site. Some of the instruments 26 commonly used in minimally invasive cardiac procedures contain complex mechanisms that enable their function during open-heart surgery. Unfortunately, these same complex inner workings can trap pockets of air or emboli that, if released in a beating heart, could be sent to the brain resulting in impairment and even death of the patient. The instrument sleeve 24 minimizes dead volume within the instrument port, thus reducing the possibility of an air bubble becoming trapped.

Once the instrument sleeve 24 is fully inserted in the channel 22, secured by the sleeve sealing mechanism 25, and the instrument 26 is fully inserted into the instrument sleeve 24 and secured by the instrument sealing mechanism 27, the instrument 26 and the gap 54 are flushed with the fluid 34. FIGS. 7-9 detail the path of fluid 34. The fluid 34 originates from the fluid source 66 and flows through the fluid inlet line 64 and passes through the check valve 70 before entering the instrument port 10 through the fluid inlet 60. The fluid 34 flows around the outer surface 56 of the instrument sleeve 24 and in the gap 54 between the inner surface 58 of the channel 22. It then flows around a proximal end 82 of the instrument sleeve 24 and into the interface 84 between the instrument sleeve 24 and the instrument 26, and then either through or around the instrument 26 (depending on the structural design of instrument 26). The fluid 34 traps any embolus found in the instrument port 10 and flushes the embolus out when the fluid 34 flows out of the instrument port 10 through the fluid outlet 72. Preferably, the fluid 34 is drawn out of the fluid flow system 32 by suction from a suction source 80, which draws fluid 34 from the fluid outlet 72 and down the suction line 76. Suction is preferred over positive pressure for forcing the fluid 34 from the fluid flow system 32, because if the positive internal pressures of the instrument port 10 exceed the pressure of the heart chamber, there is a risk of opening the end sealing mechanism 20. Applying suction actually enhances, rather than compromises, the function of the end sealing mechanism 20.

The instrument port 10 can be used in multiple orientations. In other words, if the instrument port 10 is turned upside down (i.e. the suction line 76 is located lower than the fluid inlet 60) the directionality of the suction can be reversed by switching the fluid inlet line 64 and the fluid suction line 76 such that suction is applied to the fluid inlet 60 and the fluid 34 is drawn from the fluid outlet 72. This allows the instrument port 10 to be used in any orientation.

The fluid flow system 32 can also include multiple flood lines 86 as shown in FIGS. 5a and 5b. While two flood lines 86 are shown in the figures, any number of flood lines 86 can be used. The flood lines 86 can be spaced apart from each other in any manner that enables the flood lines 86 to maintain fluid flow. Flood lines 86 are created when portions of the gap 54 between the outer surface 56 of the instrument sleeve 24 and the inner surface 58 of the channel 22 are reduced, creating any number of channel-like flood lines 86. Such a reduction in the gap 54 makes it possible to decrease the cross-talk between multiple flood lines 86 such that they can be considered independent of each other. This can be modeled in the following manner. The resistance to the flow of fluid down a circular channel (i.e. the flood line 86) can be expressed as $$R_{slot}=8L\mu/\pi b^4$$

where L is the length of the flood line 86, b is the radius of the flood line 86, and μ is the viscosity of the fluid 34. The resistance to the flow of fluid 34 through the gap 54 between the instrument sleeve 24 and the port body 12 can be expressed as $$R_{gap}=3R_{sleeve}\pi\mu/2h^3L$$

where $R_{sleeve}$ is the radius of the instrument sleeve 24, and h is the distance of gap 54. This resistance was approximated using the flat plate model since the gap 54 is much smaller than the instrument sleeve's 24 radius. If $R_{gap}/R_{slot}$ is much greater than one, flow through each of the flood lines 86 could be considered independent of each other. The dimensions applicable to the cross-talk independence calculations are shown in FIGS. 5a and 5b.

Multiple flood lines 86 can be used to introduce separate fluids 34 to different parts of the fluid flow system 32. Multiple fluid inlets 60 and multiple fluid outlets 72 plus suctions lines 76 can be used to introduce multiple fluids 34 into the flood lines 86. For example, a flushing fluid 34' can enter a first flood line 88 to flush air bubble out, and a contrast fluid 34'' can enter a second flood line 90 to act as an indicator of any remaining air bubbles, as shown in FIGS. 5a and 5b. Any other combination of fluids 34 can be used.

During use, the instrument port 10 is inserted into the patient's heart tissue 92 through an incision in the skin and tissue to the heart. The proximal end 14 of the port body 12 transects the heart, while the distal end 16 extends outside of the chest wall. The surgeon anchors the instrument port 10 to the surrounding heart tissue 92 using a purse-string suture 82 around the tissue anchoring mechanism 17, such as the ribbed heart tissue anchor 18 shown in FIG. 10. Other tissue anchoring mechanisms 17 can be used to gather and hold heart tissue 92 to the port body 12 and can include grabbing mechanisms such as a suction cup. Other suitable methods known to those of skill in the art can be used to anchor the port body 12 to the heart tissue 92. Next, the instrument 26 and instrument sleeve 24 are inserted into the channel 22 and secured as described herein. The instrument port 10 is flushed with fluid 34 using the fluid flow system 32. The instrument 26 then pushes the end sealing mechanism 20 open and the instrument 26 enters the heart tissue 92 for performing surgery in the patient. The instrument 26 is withdrawn when the surgery is complete or when the instrument is no longer needed. Upon withdrawal of the instrument 26 the end sealing mechanism 20 closes. The process can be repeated multiple times to introduce multiple instruments 26 to the site of surgery. Also, multiple instrument ports 10 can be used through different incisions in the patient's body.

The instrument port 10 of the present invention can also be used in other surgical procedures that require the introduction of instruments to a remote site in a patient's body and the prevention of emboli from entering the patient's body.

EXAMPLE

The path of the fluid 34, as shown in FIGS. 7-9, was analyzed with a MATLAB program. The geometry of five key locations in the instrument port 10 was analyzed. TABLE 1 shows the following: (1) the fluid inlet line 64, (2) the gap 54 between the instrument sleeve 24 and the port body 12, (3) the interface 84 between the instrument 26 and the instrument sleeve 24, (4) the instrument 26 cross-section, and (5) the suction line 76. Suction strength and fluid 34 properties were analyzed as well. A second suction line 76' could be added on the instrument sleeve 24 so that the interface 84 between the instrument 26 and the instrument sleeve 24 can also be flushed. In this example the instrument 26 was solid such as is found in an anchor deployment device, so that a second suction line 76' was not needed, as fluid 34 could be supplied at the fluid inlet 60 and drawn out through the fluid outlet 72. A second suction line 76' would be preferable if the instrument 26 was hollow.

A 300 mm Hg vacuum was applied to the instrument port 10, and a saline flow rate of 0.74 mL/s was found in the fluid flow system 32. The average fluid velocities in each of the five key locations were measured and are shown in TABLE 2.

The invention has been described in an illustrative manner, and it is to be understood that the terminology, which has been used, is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

We claim:

1. An instrument port for introducing an instrument into a surgical site, wherein the instrument comprises an instrument channel extending therethrough, the instrument port comprising:
    a port body including a body channel extending therethrough from an insertion end to a manipulative end of the port body, wherein the body channel is configured to receive the instrument;
    an imaging system disposed within a transparent bulb formed at the insertion end of the port body, wherein the imaging system comprises an imaging device and an illumination device;
    a flush line having an outlet at the insertion end of the port body, the flush line configured to rinse an area directly in front of the transparent bulb to provide a clear optical line of sight for the imaging device;
    a one-way valve at the insertion end of the port body, wherein the one-way valve forms a fluid-tight seal between the surgical site and the body channel and wherein the one-way valve opens when the instrument is introduced through the one-way valve into the surgical site;
    a fluid inlet at the manipulative end of the port body and in fluid communication with the body channel, wherein the fluid inlet is configured to receive fluid from a fluid source and to introduce the fluid, at the manipulative end of the port body, into the body channel;
    a fluid outlet at the manipulative end of the port body and configured to be in fluid communication with a manipulative end of the instrument channel when the one-way valve is closed, wherein the fluid outlet is configured to be connected to a suction source; and
    wherein application of suction to the fluid outlet by the suction source when the one-way valve is closed causes fluid to be drawn into the fluid inlet from the fluid source, through the body channel between an outer surface of the instrument and an inner wall of the body channel from the manipulative end to the insertion end of the port body, into an insertion end of the instrument channel, through the instrument channel towards the manipulative end, and out through the fluid outlet to remove emboli from the body channel and the instrument channel.

2. The instrument port of claim 1, further comprising a fluid inlet line configured to connect the fluid inlet to the fluid source.

3. The instrument port of claim 1, further comprising a suction line configured to connect the fluid outlet to the suction source.

4. The instrument port of claim 1, wherein the one-way valve is configured to be opened when a positive pressure is exerted on the one-way valve.

5. The instrument port of claim 4, wherein the application of suction exerts a negative pressure on the one-way valve.

6. The instrument port of claim 4, wherein the one-way valve is configured to allow an insertion end of the instrument to open the one-way valve and protrude through the insertion end of the port body.

7. The instrument port of claim 1, further comprising a control system configured to cause suction to be applied automatically after the instrument is received by the body channel.

8. The instrument port of claim 7, wherein the control system is configured to cause suction to be applied automatically when the one-way valve is closed.

9. The instrument port of claim 7, wherein the control system comprises a sensor.

10. The instrument port of claim 1, wherein the imaging system comprises an infrared imaging system.

11. The instrument port of claim 1, wherein the instrument comprises an instrument channel extending therethrough, and application of suction to the fluid outlet by the suction source causes fluid to be drawn through the instrument channel.

12. The instrument port of claim 1, wherein the one-way valve comprises a tricuspid valve.

13. The instrument port of claim 1, wherein the one-way valve comprises a magnetic seal.

14. An instrument port for introducing an instrument into a surgical site, comprising:
- a port body including a body channel extending therethrough from an insertion end to a manipulative end of the port body;
- a one-way valve at the insertion end of the port body, wherein the one-way valve forms a fluid-tight seal between the surgical site and the body channel and wherein the one-way valve opens when the instrument is introduced through the one-way valve into the surgical site;
- an instrument sleeve in slidable contact with the body channel and configured to receive the instrument, wherein the instrument sleeve includes a sleeve inlet at an insertion end of the instrument sleeve;
- a fluid inlet at the manipulative end of the port body and in fluid communication with the body channel, wherein the fluid inlet is configured to receive fluid from a fluid source and to introduce the fluid, at the manipulative end of the port body, into a gap between the instrument sleeve and the body channel; and
- a fluid outlet at the manipulative end of the port body and in fluid communication with an interface between the instrument sleeve and the instrument when the one-way valve is closed, wherein the fluid outlet is configured to be connected to a suction source; and
- wherein application of suction to the fluid outlet by the suction source when the one-way valve is closed causes fluid to be drawn into the fluid inlet, through the gap between the instrument sleeve and the body channel from the manipulative end to an insertion end of the port body, into the sleeve inlet, along the interface between the instrument sleeve and the instrument, and out through the fluid outlet to remove emboli from the body channel and the instrument sleeve.

15. The instrument port of claim 14, wherein application of suction to the fluid outlet by the suction source causes fluid to be drawn through the instrument channel.

* * * * *